(12) United States Patent
Mathison

(10) Patent No.: US 7,833,986 B2
(45) Date of Patent: *Nov. 16, 2010

(54) ANTI-INFLAMMATORY PEPTIDES

(75) Inventor: Ronald Mathison, Calgary (CA)

(73) Assignee: Salpep Biotechnology Inc., Toronto, Ontario (CA)

( * ) Notice: Subject to any disclaimer, the term of this patent is extended or adjusted under 35 U.S.C. 154(b) by 711 days.

This patent is subject to a terminal disclaimer.

(21) Appl. No.: 11/594,319

(22) Filed: Nov. 8, 2006

(65) Prior Publication Data

US 2007/0054865 A1 Mar. 8, 2007

Related U.S. Application Data

(62) Division of application No. 10/357,731, filed on Feb. 4, 2003, now Pat. No. 7,153,835.

(60) Provisional application No. 60/353,231, filed on Feb. 4, 2002.

(51) Int. Cl.
*A61K 38/06* (2006.01)
*C07K 5/08* (2006.01)
*C07K 5/083* (2006.01)
*C07K 5/087* (2006.01)

(52) U.S. Cl. .................................. 514/18; 530/331

(58) Field of Classification Search .................. None
See application file for complete search history.

(56) References Cited

U.S. PATENT DOCUMENTS

| 4,012,367 A | 3/1977 | Mazur |
| 4,880,779 A | 11/1989 | Gallaher .................. 514/15 |
| 5,635,593 A | 6/1997 | Cheronis et al. ............ 530/314 |
| 5,837,686 A | 11/1998 | Kirby et al. |
| 6,117,840 A | 9/2000 | Arrhenius et al. ............ 514/19 |
| 6,586,403 B1 | 7/2003 | Mathison et al. ............ 514/18 |
| 6,852,697 B1 | 2/2005 | Mathison et al. |

FOREIGN PATENT DOCUMENTS

| WO | 9806742 | 2/1998 |
| WO | 0063233 | 10/2000 |

OTHER PUBLICATIONS

Mathison, R. et al., Regulation of Neutrophil Function by SMR1 C-Terminal Peptides (2000), Shock, v. 13 (Suppl.): 52 (Abstract 206).
J.M. Lee, et al. J. Neuropathol. Exp. Neurol. (2002) 61(2), pp. 125-131.
Befus, D. et al., Cervical Sympathetic Nerve Trunk-Submandibular Gland Axis: Neural Control of Anti-inflammatory Peptides that Modulate Airways Inflammation (2000), Canadian Network for Neuroimmune Biology Symposium, Winnipeg, Manitoba, Jun. 9-12, 2000.
Befus, D. et al., C-terminal Peptides of the Prohormone SMR1 Inhibit Allergic Information in the Airways (2000), CSI 2000, Quebec, Canada.
Befus, D. et al., Inhibition of Allergic Inflammation C-terminal Peptides of SMR1 (2000), CIA, Japan.
Davison, J.S. et al., Salivary Gland Peptides: Their role in Anaphylaxis and LPS-induced Inflammation, (2000), CANIB Symposium, Manitoba, Jun. 9-12, 2000.
Déry, R. et al., A Novel Peptide Isolated from Prohormone Smr1 Inhibits Allergic Inflammation of the Airways (2000), American Thoracic Society, Toronto, Canada, May 5-10, 2000.
Déry, R. et al., Inhibition of Airway Inflammation by feG: A C-Terminal Peptide Isolated from Rat Submandibular Gland Prohormone Smr1 (1999), Alberta Respiratory Disease Symposium, Banff, Alberta, Oct. 22-24, 1999.
Hwang, S. et al., Inhibition of Gene Expression in Human Cells Through Small Molecule-RNA Interactions (1999), PNAS, v. 96, pp. 12997-13002.
Llinas—Brunet et al., (1999), J.Med.Chem., v.42, pp. 722-729.
Mathison R: The Submandibular Glands: a role in homeostasis and allostasis. (1995), Biomedical Reviews, v. 4, pp. 61-69.
Mathison RD. et al., . Reduction in cardiovascular anaphylaxis by submandibular gland peptide-T (1995), Proc. West. Pharmacol. Soc., v. 40, pp. 73-74.
Mathison, R. et al., A Novel Submandibular Gland Peptide Protects Against Endotoxic and Anaphylactic Shock (1997), Am. J. Physiol., v. 273: R1017-R1023.
Mathison, R. et al., Attenuation of Intestinal and Cardiovascular Anaphylaxis by the Salivary Gland Tripeptide FEG and Its D-Isomeric Analog feG (1998), Peptides, v. 19, pp. 1037-1042.

(Continued)

*Primary Examiner*—Andrew D Kosar
(74) *Attorney, Agent, or Firm*—Myers Bigel Sibley & Sajovec, P.A.

(57) ABSTRACT

Methods for inhibiting an inflammatory reaction in a mammal and pharmaceutical compositions are provided. The methods comprise administering to the mammal an effective amount of a peptide of the formula:

$X^1$-$X^2$-$X^3$ wherein $X^1$ is selected from the group consisting of 2-amino-hexanoic acid; 2-amino-heptanoic acid; 2-amino-octanoic acid; cyclohexyl-substituted 2-amino-ethanoic acid, 2-amino-propanoic acid or 2-amino-butanoic acid and methionine; $X^2$ is an acidic amino acid; and $X^3$ is an aliphatic amino acid; or of a peptide of the formula: $X^4$-$X^5$ wherein $X^4$ is an aromatic or aliphatic amino acid; and $X^5$ is an acidic amino acid.

27 Claims, 10 Drawing Sheets

OTHER PUBLICATIONS

Mathison, R. et al., Inhibition of Leucocyte Rolling by Submandibular Gland Peptide-T (CGP-T),(1999) Proc. West. Pharmacol. Soc., v. 42, pp. 39-40.

Mathison, R. et al., Neuroendocrine Regulation of Inflammation and Tissue Repair by Submandibular Gland Factors (1994), Immunology Today, v. 15, p. 527.

Mathison, R. et al., Reduction of endotoxin-induced leukocyte activation in the rat intestine by a D-isomeric analogue of salivary gland tripeptide FEG. (2000), Abstract: American Gastroenterology Association, San Diego, California, May 21-24, 2000.

Mathison, R. et al., Removal of the Submandibular Glands Increases the Acute Hypotensive Response to Endotoxin (1993), Circ. Shock, v. 39, p. 52.

Mathison, R. et al., Submandibular Gland Peptide-T (SGP-T) : Modulation of Endotoxic and Anaphylactic Shock, (1997), Drug Devel. Res., v. 42, pp. 164-171.

Mathison, R. et al., Submandibular Gland Peptide-T (SGP-T) Inhibits Intestinal Anaphylaxis (1997), Dig. Dis. Sci., v. 42, pp. 2378-2383.

Mathison, R. et al., The D-isomeric Analog of Salivary Gland Tripeptide FEG Reduces Endotoxin Induced Cell Activation in the Rat Intestine (1999), Falk Symposium: Neurogastroenterology—From the Basics to the Clinics, Jun. 21-22, 1999.

Mathison, R. et al., The Role of Submandibular Gland Peptide feG in Anaphylaxis-Induced Cardiac Inflammation (2000), Shock, v. 13 (Suppl.): 52.

Munch, G. et al., Amino acid specificity of glycation and protein-AGE crosslinking reactivities determined with a dipeptide SPOT library (1999), Nature Biotech., v. 17, pp. 1006-1010.

Nkemdirim M. et al., Modulation of neutrophil activity by submandibular gland peptide-T (SGP-T). (1998), Pol. J. Pharmacol. v. 50: 417-424.

Ramaswamy K. et al., Marked Antiinflammatory Effects of Decentralization of the Superior Cervical Ganglia (1990), J. Exp. Med., v. 172, pp. 1819-1830.

Schullek, J. R. et al., A High-Density Screening Format for Encoded Combinatorial Libraries: Assay Miniaturization and Its Application to Enzymatic Reactions (1997), Anal. Biochem., v. 246, pp. 20-29.

Slootstra, Structural aspects of antibody-antigen interaction revealed through small random peptide libraries (1996), Molecular Diversity, v. 1, pp. 87-96.

Turesin, F. et al., The Role of Submandibular Gland Peptide feG in Anaphylaxis-Induced Cardiac Inflammation (2000), Shock, v. 13 (Suppl.): 52.

Dery, R.E., et al., Inhibition of Allergic Inflammation by C-Terminal Peptides of the Prohormone Submandibular Rat 1 (SMR-1), (2001), Int. Arch. Allergy Immunol., v. 124, pp. 201-204.

Grossmann, C. et al., Partitioning of Low Molecular Combination Peptides in Aqueous Two-Phase Systems of Poly(ethylene glycol) and Dextran in the Presence of Small Amounts of $K_2HPO_4/KH_2PO_4$ Buffer at 293: experimental results, (1998), Biotechnology and Bioengineering, v. 60, no. 6, pp. 699-711.

Liakopoulou-Kyriakides, M. et al., Effect of Leu-(ASP, ASN, GLU, GLN) Dipeptides on Platelet Aggregation in vitro (1990), Biochemistry International, v. 22, No. 4, pp. 617-625.

Mathison, R. et al., Attenuation of Intestinal and Cardiovascular Anaphylaxis by the Salivary Gland Tripeptide FEG and its D-isomeric Analog feG, (1998), Peptides, v. 19, no. 6, pp. 1037-1042.

Metwally, E. et al., Submandibular Gland Tripeptide FEG (Phe-Glu-Gly) and Analogues: keys to structure Determination, (2002), Peptides, v. 23, pp. 193-199.

Schon, I. et al., Pentagastrin Analogs Containing α-aminooxy Acids, II, (1978), Hoppe-Seyler's Z. Physiol. Chem. Bd. 359, pp. 897-916.

Tan, D. et al., The Carboxamide feG(NH2) Inhibits Endotoxin Perturbation of Intestinal Motility, (2000), European Journal of Pharmacology v. 409, p. 203-205.

European Search Report for corresponding European Application No. EP 09002264.1, dated Aug. 12, 2009 (12 pages).

Ragusa et al. "Substrate Recognition and Selectivity of Peptide Deformylase. Similarities and Differences with Metzincins and Thermolysin" *Journal of Molecular Biology* 289 (5):1445-1457 (1999).

A.

B.

ANTI-INFLAMMATORY PEPTIDES

RELATED APPLICATION INFORMATION

This application claims priority as a divisional application from U.S. application Ser. No. 10/357,731, filed Feb. 4, 2003, now U.S. Pat. No. 7,153,835 which claims the benefit of U.S. Provisional Application No. 60/353,231, filed Feb. 4, 2002; the disclosures of which are incorporated herein by reference in their entireties.

FIELD OF THE INVENTION

This invention relates to dipeptides and tripeptides with anti-inflammatory activity and to methods and compositions for treating inflammatory reactions, including allergic reactions.

BACKGROUND OF THE INVENTION

Immediate or Type 1 allergic reactions generally occur, in susceptible humans and animals, immediately following contact with an antigen, which is referred to as the allergen. Such reactions may have long term consequences. Type I allergic reactions are largely attributed to IgE antibodies, although IgG antibodies can participate in and modulate them (Dombrowicz et al, 1998; Ujike et al, 1999). An allergic reaction is generally caused by the activation of a subpopulation of immune cells, the mast cells and basophils. When an antigen reacts with IgE antibody receptors on the surface of a cell, chemical mediators initiate the allergic reaction by acting on adjacent immune, epithelial, endothelial and smooth muscle cells and promote, in a longer term, the influx of other inflammatory and immune cells (neutrophils, eosinophils, monocytes, lymphocytes) into the affected tissue. This influx of inflammatory cells predisposes the patient to recurrent, and sometimes delayed or prolonged, allergic or hypersensitivity reactions and is frequently associated with non-reversible remodelling of the tissue. Type 1 allergic reactions are identified according to the location in which they occur, e.g. asthmatic reactions occur in the lungs, rhinitis in the nose, conjunctivitis in the eyes, atopic dermatitis in the skin, systemic allergic reactions in the circulation and intestinal reactions in the gastrointestinal system.

Asthma can be defined clinically as a condition of intermittent, reversible airways obstruction; asthma manifests itself as several clinical entities: allergic asthma, bronchial asthma, exercise induced asthma (EIA), chemical induced asthma, and status asthmaticus. Asthma can be divided into two types. Extrinsic asthma is generally triggered by external agent such as allergens (dust mites, pollen, stings, drugs, or foods), and is commonly diagnosed in early life. Intrinsic asthma, which is allergic-like and generally develops later in life, can be triggered by congested and inflamed tissues, infection, common cold viruses (RSV, parainfluenza, rhinovirus), endogenous catecholamines (e.g. adrenaline), drugs (e.g. aspirin), cold air, stress or exertion, various irritants (cigarette smoke, burning leaves, perfumes, strong odors) and some food intolerance. Intrinsic asthma occurs without the participation of an allergic trigger by specific antibodies against an allergen.

Bronchial asthma is usually a chronic (long-term) disease affecting the bronchial tubes (bronchi and/or airways) of the lungs. The symptoms of asthma are the result of constriction or narrowing of irritable bronchial tubes resulting in wheezing and difficulty in breathing. This constriction of the airways, caused by bronchial tube muscle spasm and narrowing due to inflammation, is most frequently provoked by antigen-induced release of histamine, leukotrienes and other chemical mediators from mast cells. With intrinsic asthma, these mediators are released without an allergic trigger. The net result of the asthmatic attack is muscle spasm, inflammation, edema (swelling), and increased mucus production within the bronchi. Both extrinsic and intrinsic asthmatic reactions generate symptoms within 15-30 minutes of exposure (immediate response) which generally subside within an hour. In some individuals, a delayed response (late phase reaction) occurs 3-4 hours following the immediate or initial response. It should be noted, however, that the timing of these reactions exhibits marked variability between patients and can be shorter or longer in onset and duration. The late phase reaction, which probably develops from an inflammatory reaction, may last many hours or days and is frequently associated with increased bronchial hyperreactivity or persistent airway hyperresponsiveness. As a consequence, the bronchioles become irritable and hyperresponsive, rendering the individual more sensitive to a variety of inhaled irritants other than the allergen.

Rhinitis, allergic conjunctivitis and atopic dermatitis are inflammations of the nasal mucosa, eyes and skin, respectively, often due to allergens such as pollen, dust or other airborne substances.

Anaphylactic shock, the most severe form of allergy, is a medical emergency. It is often severe and can sometimes provoke a fatal systemic reaction in a previously sensitized human or animal upon exposure to a specific antigen, such as nuts, wasp or bee venom or penicillin. Anaphylactic shock is characterized by respiratory symptoms, fainting, itching, urticaria, swelling of the throat or other mucous membranes and/or a sudden decline in blood pressure. Symptoms of anaphylactic shock include dizziness, loss of consciousness, laboured breathing, swelling of the tongue, blueness of the skin, bronchospasm, low blood pressure, and death. Anaphylactic reactions can also cause modification of heart function and are associated with an increase in neutrophil influx into the heart tissue (Turesin et al, 2000). This inflammation of the heart is effected by the leukocyte adhesion cascade.

For the most part, the available drugs for treating asthma block or neutralize the effects of the release of inflammatory mediators such as histamine, prostaglandins, leukotrienes, platelet activating factor (PAF) and chemotactic factors for monocytes, neutrophils and eosinophils. These mediators activate smooth muscle, causing bronchial constriction, and act on adjacent immune, epithelial and endothelial cells to facilitate and amplify the inflammatory response. The drugs currently available for treating asthma include the beta-adrenergics, corticosteroids, anti-leukotrienes, anti-cholinergics, xanthines and, less frequently non-steroidal anti-inflammatory drugs, (NSAIDS).

These drugs, when used properly, provide good management of asthma. A significant number of asthma sufferers, however are poorly controlled and a need for improved anti-asthmatic drug therapy remains.

Anti-inflammatory peptides derived from the salivary gland have been described previously. These include submandibular gland peptide-T (SGP-T), which inhibits lipopolysaccharide-induced hypotension at doses as low as 1 µg/kg (Mathison et al., (1997) Amer. J. Physiol., v. 273, p. R1017) and has also been shown to inhibit systemic and intestinal Type 1 hypersensitivity reactions (Befus et al., (1997) Int. Arch. Allergy Immunol., v. 113, p. 337; Mathison et al, (1997) supra and Proc. West Pharmacol. Soc., v. 40, p. 73). Further studies demonstrated that tripeptide or larger fragments of SGP-T also have significant anti-inflammatory activity (International Patent Application WO 98/06742).

SUMMARY OF THE INVENTION

The present invention provides novel peptides which are potent inhibitors of inflammatory reactions in mammals.

The di- and tripeptides of the invention have been shown to inhibit inflammatory reactions due to a wide variety of causes and can be used to treat inflammatory reactions and disorders involving an inflammatory reaction in general, in human and non-human mammals. The peptides have human and veterinary pharmaceutical uses. They may be formulated as pharmaceutical compositions or used as food additives.

In accordance with one embodiment, the invention provides a method of inhibiting an inflammatory reaction in a mammal comprising administering to the mammal an effective amount of a peptide of the formula:

$X^1$-$X^2$-$X^3$ wherein $X^1$ is selected from the group consisting of 2-amino-hexanoic acid; 2-amino-heptanoic acid; 2-amino-octanoic acid; cyclohexyl-substituted 2-amino-ethanoic acid, 2-amino-propanoic acid or 2-amino-butanoic acid and methionine;

$X^2$ is an acidic amino acid; and $X^3$ is an aliphatic amino acid;

or of a peptide of the formula:

$X^4$-$X^5$ wherein $X^4$ is an aromatic or aliphatic amino acid; and $X^5$ is an acidic amino acid.

In accordance with a further embodiment, the invention provides a method of treating asthma in a mammal comprising administering to the mammal an effective amount of a peptide of the formula:

$X^1$-$X^2$-$X^3$ wherein $X^1$ is selected from the group consisting of 2-amino-hexanoic acid; 2-amino-heptanoic acid; 2-amino-octanoic acid; cyclohexyl-substituted 2-amino-ethanoic acid, 2-amino-propanoic acid or 2-amino-butanoic acid and methionine;

$X^2$ is an acidic amino acid; and $X^3$ is an aliphatic amino acid;

or of a peptide of the formula:

$X^4$-$X^5$ wherein $X^4$ is an aromatic or aliphatic amino acid; and $X^5$ is an acidic amino acid.

In accordance with a further embodiment, the invention provides a peptide of the formula: $X^1$-$X^2$-$X^3$ wherein $X^1$-$X^2$-$X^3$ wherein $X^1$ is selected from the group consisting of 2-amino-hexanoic acid; 2-amino-heptanoic acid; 2-amino-octanoic acid; cyclohexyl-substituted 2-amino-ethanoic acid, 2-amino-propanoic acid or 2-amino-butanoic acid and methionine;

$X^2$ is an acidic amino acid; and $X^3$ is an aliphatic amino acid.

In accordance with a further embodiment, the invention provides a peptide of the formula: $X^4$-$X^5$ wherein $X^4$ is an aromatic or aliphatic amino acid; and $X^5$ is an acidic amino acid.

In accordance with a further embodiment, the invention provides a pharmaceutical composition comprising a peptide as described above and a pharmaceutically acceptable carrier.

In accordance with a further embodiment, the invention provides use of a peptide as described above for the preparation of a medicament for inhibiting an inflammatory reaction or for treating asthma.

SUMMARY OF THE DRAWINGS

Certain embodiments of the invention are described, reference being made to the accompanying drawings, wherein.

DETAILED DESCRIPTION OF THE INVENTION

Figure 1:
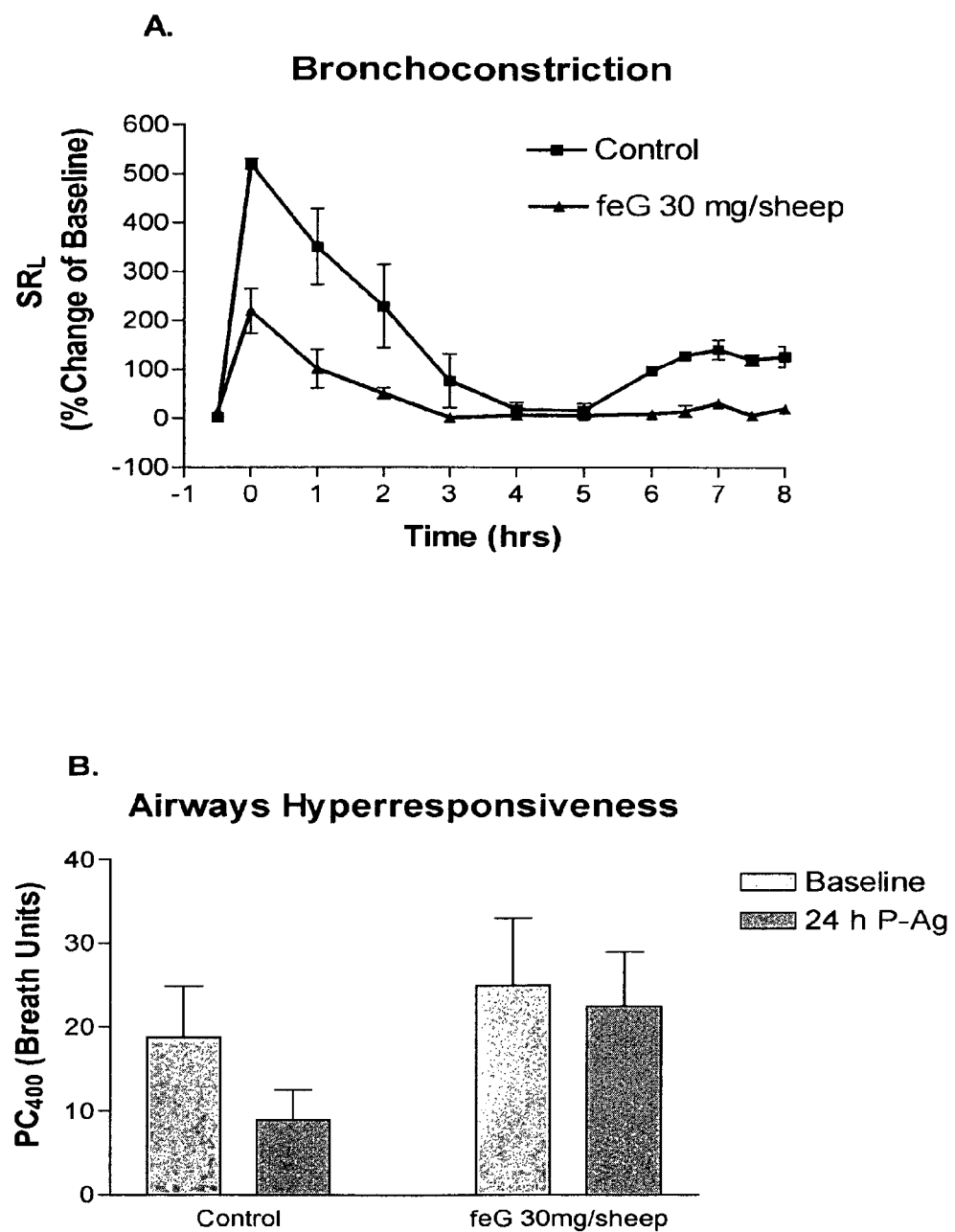
FIG. 1A shows the effect of aerosol feG treatment on antigen-induced airways bronchoconstriction in sheep, expressed as % change in $SR_L$, over time (hours) after antigen challenge. Values are expressed as mean±SEM for two animals.
FIG. 1B shows the effect of aerosol feG on antigen-induced airways hyperreponsiveness in sheep, expressed as the number of breaths (Breath Units) required to increase airways resistance by 400% ($PC_{400}$), before (Baseline) and at 24 h Post-antigen challenge (24 h P-Ag). Values are expressed as mean±SEM for two animals.

The amino acids which are components of normal mammalian proteins are referred to herein by the conventional one letter or three letter codes. When the one letter code is used, L-isomeric forms of amino acids are identified by capital letters and D-forms by lower case letters, e.g. L-phenylalanine: F; D-phenylalanine: f. Reference to an amino acid without explicit indication of isomeric form refers to the L form.

Other amino acids referred to herein are identified as follows:

| Amino Acid | Abbreviation | Formula |
| --- | --- | --- |
| β alanine | β Al | $(NH_2)$—$CH_2$—$CH_2$—COOH |
| γ amino butyric acid | γ Abu | $(NH_2)$—$(CH_2)$—$_3$—COOH |
| L-cyclohexylalanine | Cha | C6H11—$CH_2$—$CH(NH_2)$—COOH |
| D-cyclohexylalanine | cha | |
| homoserine | Hse | HO—$(CH_2)_2$—$CH(NH_2)$—COOH |
| norleucine | Nle | $CH_3$—$(CH_2)_3$—$CH(NH_2)$—COOH |
| norvaline | Nval | $CH_3$—$(CH_2)_2$—$CH(NH_2)$—COOH |
| phenyl glycine | Phg | C6H5—$CH(NH_2)$—COOH |
| sarcosine | Sar | $NH(CH_3)$—$CH_2$—COOH |

An "acidic amino acid" is an amino acid which has a side chain containing one or more carboxyl groups.

Beginning with the peptide FEG, which has been shown to have anti-inflammatory activity, a number of analogues of the peptide have been synthesised, substituting one or more amino acids with a different amino acid, in either D or L form, and the anti-inflammatory activity of these analogues has been examined. Based on these studies, and the unexpected results of various substitutions, the invention provides new groups of peptides which are potent modulators of inflammatory reactions in mammals.

Although earlier studies suggested that the N-terminal amino acid of FEG analogues had to be aromatic for activity, it has been found unexpectedly that the N-terminal amino acid may be aliphatic. It has further been found unexpectedly that a dipeptide may be sufficient for anti-inflammatory activity.

The invention provides anti-inflammatory peptides of the formula: $X^1$-$X^2$-$X^3$ wherein $X^1$ is selected from the group consisting of 2-amino-hexanoic acid; 2-amino-heptanoic acid; 2-amino-octanoic acid; cyclohexyl-substituted 2-amino-ethanoic acid, 2-amino-propanoic acid or 2-amino-butanoic acid, and methionine; $X^2$ is an acidic amino acid; and $X^3$ is an aliphatic amino acid.

Of the cyclohexyl-substituted amino acids, 2-amino-2-cyclohexyl-ethanoic acid, 2-amino-3-cyclohexyl-propanoic acid, 2-amino-3-cyclohexyl-butanoic acid and 2-amino-4-cyclohexyl-butanoic acid are preferred.

Especially preferred amino acids for position $X^1$ are 2-amino-3-cyclohexyl-propanoic acid (cyclohexylalanine), 2-amino-hexanoic acid (norleucine) and methionine.

$X^2$ is preferably glutamic acid and $X^3$ is preferably glycine, methionine, isoleucine, alanine, β-alanine, sarcosine or γ amino butyric acid.

The invention further provides anti-inflammatory peptides of the formula: $X^4$-$X^5$ wherein $X^4$ is an aromatic or aliphatic amino acid; and $X^5$ is an acidic amino acid.

$X^4$ is preferably phenylalanine, norleucine, cyclohexylalanine, methionine or tyrosine and $X^5$ is preferably glutamic acid.

One or more of the amino acids of the peptides of the invention may be D-amino acids.

In a further embodiment, and by analogy with previous findings on amidated FEG and feG, the tripeptides and dipeptides of the invention may be used in amidated form, i.e. the C-terminal amino acid of the peptide is amidated. Such amidated peptides may be more stable in the mammalian body than the carboxy terminal peptides.

In a further embodiment, in the peptides of the invention, the amide of the N-terminal amino acid may be substituted with a straight chain lower alkyl group of 1 to 3 carbons. Where methionine is the N-terminal amino acid, it may be thio-substituted. Cyclohexyl-containing peptides may be lower alkyl substituted on the cyclohexyl ring. Lower alkyl substitution is preferably methyl substitution.

An inflammatory reaction in a mammal is a protective response against a variety of damaging or potentially damaging agents. Such agents include allergens, toxins, bacteria, viruses, parasites and fungi.

Inflammatory reactions are associated with increased vascular permeability and blood flow, migration of leukocytes to the site of the inflammatory reaction, and release of vasodilatory, cytotoxic and tissue repair molecules.

Depending on the tissue or organ involved, an inflammatory reaction will lead to different symptoms. For example, an inflammatory reaction in the lungs may lead to pulmonary inflammation, bronchoconstriction and airway obstruction.

Inflammatory reactions are involved in the symptomatology of asthma, whether triggered by external agents such as allergens, as in extrinsic asthma, or by non-allergen factors, as in intrinsic asthma.

Inflammatory response syndrome (IRS) involves a severe and widespread inflammatory reaction affecting multiple organs and tissue. IRS occurs as a result of extensive tissue damage and necrosis or the invasion of microorganisms, with the release of chemical mediators or cellular by-products such as the cytokines, lipid metabolites and autocoids. These mediators can be released as a result of tissues and cells affected by infections, shock (endotoxemia, blood loss, blunt trauma), hypoxemia, radiation, burns, organ transplants, graft rejections. The inflammatory IRS is primarily responsible for the development of organ dysfunctions, such as acute lung injury, acute respiratory distress syndrome (ARDS), damage to gastrointestinal dysfunction (ileus, changes in permeability, pancreatitis like problems), and dysfunctions of the kidney, heart, liver and brain.

An acute and overwhelming reaction to an allergen may lead to anaphylactic shock, where many organs and systems of the body are affected by the inflammatory reaction.

Exposure to an allergen can cause an inflammatory reaction in the intestines which, in severe cases, can cause intestinal anaphylaxis or even systemic anaphylaxis. Cardiac inflammation may result from ischemia or as a component of reperfusion injury.

Inflammatory reactions also include endotoxic reactions, immunological reactions and hypersensitivity reactions, including Type I, Type II and Type III hypersensitivity reactions.

Inflammatory reactions also include endotoxic reactions to lipopolysaccharide components of gram negative bacteria.

Type I hypersensitivity reactions or allergic reactions are typically immunoglobulin E-mediated and occur in many allergic disorders, including allergic rhinitis, allergic conjunctivitis, atopic dermatitis, extrinsic asthma, and some cases of urticaria, gastrointestinal reactions to food and systemic anaphylaxis.

Type II and Type III hypersensitivity reactions are generally mediated by antibodies other than IgE, and can involve immunoglobulin G-mediated reactions, as well as those using other immunoglobulins. Type II reactions are cytotoxic reactions resulting when antibody reacts with antigenic components of a cell or tissue elements or with antigen or hapten that is coupled to a cell or tissue. The antigen-antibody reaction may activate certain cytotoxic cells (e.g. killer T cells or macrophages) to produce antibody-dependent cell-mediated cytotoxicity. Type II reactions are involved in disorders including hemolytic anaemias, antibody-induced thrombocytopenic purpura, leukopenia, pemphigus, pemphigoid, Goodpasture's syndrome, pernicious anaemia, incompatible blood transfusions, neonatal thrombocytopenia and multisystem hypersensitivity diseases such as scleroderma. Type III reactions are immune complex (IC) reactions resulting from deposition of soluble circulating antigen-antibody ICs in vessels or tissue, and are involved in disorders including serum sickness due to serum, drugs or viral hepatitis antigen, scleroderma rheumatoid arthritis, polyarteritis, cryoglobulinemia, hypersensitivity pneumonitis, bronchopulmonary aspergillosis, acute glomerulonephritis, chronic membrane proliferative glomerulonephritis and related renal diseases.

The results described herein indicate that the compounds of the invention are effective in inhibiting both inflammatory reactions involving Type I hypersensitivity reactions (e.g. allergic asthma, intestinal response to antigen) and inflammatory reactions involving Type III hypersensitivity reactions (e.g. vascular permeability and cutaneous anaphylaxis).

In any disorder involving an inflammatory reaction, the subject's symptoms can be ameliorated and the disorder treated by administering an anti-inflammatory agent to the subject to inhibit the reaction. Although it is not yet known by what mechanism the peptides of the invention interfere with inflammatory reactions, the peptides of the invention may be used to inhibit inflammatory reactions generally. It is clear from the studies described herein that they are effective to inhibit inflammatory reactions involving a wide variety of causes, including allergen-induced and non-allergen-induced asthma, allergen-induced and food intolerance-related intestinal disorders, anaphylactic shock, endotoxic reactions and inflammatory response syndrome.

The compounds of the invention may also be used as veterinary pharmaceuticals, for the treatment of a variety of diseases and conditions common to mammals other than humans. All animals can experience Types I, II and III hypersensitivity reactions, immunological reactions, and the other types of inflammatory reactions described herein.

One of the most common conditions affecting household pets, including cats and dogs, is allergy, which can affect all major organ systems. These allergies are characterized by itching of the skin, either localized or generalized, hyper-responsive (over-reactive) airways, coughing, sneezing and/or wheezing and discharge from nose and/or ears or vomiting or diarrhea. Non-human mammals which may be treated with the methods and compositions of the invention include dogs, cats, mice, rats, rabbits, horses, cows, sheep and other domestic pets and farm animals.

The invention therefore provides new pharmaceutical compositions and methods for inhibiting an inflammatory reaction in human and non-human mammals, comprising administering to the mammal an effective amount of a peptide as described herein. These compositions and methods can be employed to treat a wide variety of disorders involving an inflammatory reaction, including asthma, rhinitis, conjunctivitis, atopic dermatitis, intestinal anaphylaxis, allergen-induced and food intolerance related intestinal disorders and systemic allergic reactions.

The peptides of the invention can also be employed to treat pulmonary inflammation and bronchoconstriction and immunological reactions and to inhibit chemotaxis of inflammatory cells, including neutrophils, into an inflammatory site.

An "effective amount" means an amount sufficient to produce a significant inhibition of an inflammatory reaction, as evidenced, for example, by an observable amelioration of one or more symptoms produced by the inflammatory reaction or by a reduction in one or more of the above-described indicia of inflammatory reactions, such as increased vascular permeability, leukocyte migration, etc.

Peptides in accordance with the invention may be prepared by any suitable peptide synthetic method, as are known to those of skill in the art.

Chemical synthesis may be employed; for example standard solid phase peptide synthetic techniques may be used. In standard solid phase peptide synthesis, peptides of varying length can be prepared using commercially available equipment. This equipment can be obtained, for example, from Applied Biosystems (Foster City, Calif.). The reaction conditions in peptide synthesis are optimized to prevent isomerization of stereochemical centres, to prevent side reactions and to obtain high yields. The peptides are synthesized using standard automated protocols, using t-butoxycarbonyl-alpha-amino acids, and following the manufacture's instructions for blocking interfering groups, protecting the amino acid to be reacted, coupling, deprotecting and capping of unreacted residues. The solid support is generally based on a polystyrene resin, the resin acting both as a support for the growing peptide chain, and as a protective group for the carboxy terminus. Cleavage from the resin yields the free carboxylic acid. Peptides are purified by HPLC techniques, for example on a preparative C18 reverse phase column, using acetonitrile gradients in 0.1% trifluoroacetic acid, followed by vacuum drying. The peptides of the invention can also be produced by liquid phase peptide chemistry.

Peptides may also be produced by recombinant synthesis. A DNA sequence encoding the desired peptide is prepared and subcloned into an expression plasmid DNA. Suitable mammalian expression plasmids include pRC/CMV from Invitrogen Inc. The gene construct is expressed in a suitable cell line, such as a Cos or CHO cell line and the expressed peptide is extracted and purified by conventional methods. Suitable methods for recombinant synthesis of peptides are described in Sambrook et al., (1989), "Molecular Cloning" Cold Spring Harbor, Lab. Press, Cold Spring Harbor, N.Y. Derivatives of a peptide may be prepared by similar synthetic methods. Examples of side chain modifications contemplated by the present invention include modification of amino groups such as by reductive alkylation by reaction with an aldehyde followed by reduction with $NaBH_4$; amidation with methylacetimidate; acetylation with acetic anhydride; carbamylation of amino groups with 2, 4, 6, trinitrobenzene sulfonic acid (TNBS); alkylation of amino groups with succinic anhydride and tetrahydrophthalic anhydride; and pyridoxylation of lysine with pyridoxal-5'-phosphate followed by reduction with $NaBH_4$.

The guanidino group of arginine residues may be modified by the formation of heterocyclic condensation products with reagents such as 2,3-butanedione, phenylglyoxal and glyoxal.

The carboxyl group may be modified by carbodiimide activation via acylisourea formation followed by subsequent derivatisation, for example, to a corresponding amide.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid-, 5-butylglycine, norvaline, phenylglycine, ornithine, sarcosine, 4-amino-3-hydroxy-6-methylheptanoic acid, 2-thienyl alanine and/or D-isomers or amino acids.

Synthesized peptides may be screened for their anti-inflammatory activity by one of the assay systems described herein. The assay selected will depend on the biological activity of interest in each case. For example, peptides may be screened for their effectiveness in inhibiting vascular permeability changes by the method described in Example 3 or for their effectiveness in inhibiting antigen-induced airway bronchoconstriction, as described in Example 2.

The peptides of the invention may be administered therapeutically by injection or by oral, nasal, buccal, sub-lingual, rectal, vaginal, transdermal or ocular routes in a variety of formations, as in known to those in the art.

For oral administration, various techniques can be used to improve stability, based for example on chemical modification, formulation and use of protease inhibitors. Stability can be improved if synthetic amino acids are used, such as peptides or betidamino acids, or if metabolically stable analogues are prepared.

Formulation may be, for example, in water/oil emulsion or in liposomes for improved stability. Oral administration of peptides may be accompanied by protease inhibitors such as aprotinin, soybean trypsin inhibitor or FK-448, to provide protection for the peptide. Suitable methods for preparation of oral formulations of peptide drugs have been described, for example by Saffran et al., (1979), Can. J. Biochem., v. 57, pp. 548-553; Lundin et al., (1986), Life Sci., v. 38, pp. 703-709, and Vilhardt et al., (1986), Gen. Pharmacol., v. 17, pp. 481-483.

Due to the high surface area and extensive vascular network, the nasal cavity provides a good site for absorption of both lipophilic and hydrophilic drugs, especially when coadministered with absorption enhancers. The nasal absorption of peptide-based drugs can be improved by using aminoboronic acid derivatives, amastatin, and other enzyme inhibitors as absorption enhancers and by using surfactants such as sodium glycolate, as described in Amidon et al., (1994), Ann. Rev. Pharmacol. Toxicol., v. 34, pp. 321-341. The transdermal route provides good control of delivery and maintenance of the therapeutic level of drug over a prolonged period of time, Amidon et al., (1994), Ann. Rev. Pharmacol. Toxicol., v. 34, pp. 321-341 and Choi et al., (1990), Pharm. Res., v. 7, pp. 1099-1106. A means of increasing skin permeability is desirable, to provide for systemic access of peptides. For example, iontophoresis can be used as an active driving force for charged peptides or chemical enhancers such as the nonionic surfactant n-decylmethyl sulfoxide (NDMS) can be used.

Peptides may also be conjugated with water soluble polymers such as polyethylene glycol, dextran or albumin or incorporated into drug delivery systems such as polymeric matrices to increase plasma half-life.

More generally, formulations suitable for particular modes of administration of peptides are described, for example, in Remington's Pharmaceutical Sciences (Ed. Gennaro, A. R., (2000), 20$^{th}$ Edition, Williams & Wilkins PA, U.S.A.).

The particular dosage required in a given subject can be determined by the attending physician. A starting dosage in the range of 1 µg-1000 µg peptide/kg body weight can be employed, with adjustment of the dosage based on the response of a particular subject, as understood by those of ordinary skill in the art.

The peptides of the invention may also be formulated as food supplements by their addition to food products or beverage products. The use of peptides as food additives and their incorporation into food or beverage products is well known to those of skill in the food processing art. Where the peptides contain only natural amino acids, these products are attractive to those who favour natural medicines and natural health products.

EXAMPLES

The examples are described for the purposes of illustration and are not intended to limit the scope of the invention.

Methods of chemistry, protein and peptide biochemistry and immunology referred to but not explicitly described in this disclosure and examples are reported in the scientific literature and are well known to those skilled in the art.

Example 1

Effects of Peptides on Antigen-Induced Contraction of Sensitized Rat Ileum

For this in vitro motility study, peptides were prepared by conventional methods at the Protein Synthesis Facilities, University of Calgary, Calgary, Alberta, or by Core Laboratories, Queen's University, Kingston, Ontario, and examined for their inhibitory effects on an anaphylactic reaction provoked by antigen on intestinal segments isolated from ovalbumin sensitized rats. The procedures described by Mathison et al. (1997), (supra) were followed with slight modifications. Sprague-Dawley rats were sensitized to 1 mg ovalbumin (OA) and 50 ng pertussis toxin (Sigma Chemical, St. Louis, Mo.) (Kosckea et al, 1994, Am. J. Physiol., v. 267, pG745). Four to six weeks following sensitization, the terminal ileum was excised and 2 cm sections were mounted in 20 ml organ baths under 0.75 g of tension and the isometric force generated by OA and urecholine (Frosst, Kirkland, QC) was measured using a Grass Force Displacement Transducer FT03 (Quincy, Mass.). The tissues were washed several times in Krebs and allowed to equilibrate for 15 minutes. Anti-anaphylactic properties of the peptides were determined by adding 10 µg of peptide to a bath and incubating for 10 min. Tissue segments were washed, the baseline reestablished, and then challenged with 1 mg of the OA antigen. OA contractile response was measured at peak contraction. Tissues were washed and peak contractile response obtained by adding urecholine to a concentration of $10^{-5}$M. The mucosa was then scraped from the tissue, the mass of the remaining muscle determined, and the tension calculated in gram force per gram wet tissue. Results were expressed as the ratio of OA induced contractile response to urecholine induced contractile response. To obtain the relative activity the OA/URE ratio for each peptide was expressed as a percent of control.

The results are shown in Table 1. The addition of antigen (OA) induced a slow tonic contraction of the intestinal (ileal) segments which peaked within 2 to 3 minutes before slowly receding to the baseline tension over 4 to 5 minutes. Urecholine (URE) produced a rapid tonic contraction that reached its maximum in 10 to 15 seconds. The tripeptide analogues did not alter the contractile response to URE (not shown), which allowed the use of the OA/URE ratio as a measure of the anti-anaphylactic responses of the peptide. The OA/URE ratio in untreated tissues was 0.26±0.02, which indicates that the sensitizing antigen caused a contractile response that was 26% of that of urecholine.

Example 2

Treatment of Asthmatic Reactions in Sheep

Animal Preparation: Experiments were performed as described by Abraham et al. (2000), Am. J. Respir. Crit. Care Med., v. 162, p. 603. Allergic sheep, weighing 27 to 50 kg, had previously been shown to have a natural allergic cutaneous reaction to 1:1000 or 1:10,000 dilutions of *Ascaris suum* extract (Greer Diagnostics, Lenoir, N.C.) and to develop both early and late bronchial responses ("dual responders") to inhaled *Ascaris suum* antigen (Abraham et al, 1983, Am. Rev. Respir. Dis., v. 128, p. 839). The sheep were conscious and restrained in a modified shopping cart in the prone position with their heads immobilized. Topical anesthesia (2% lidocaine) was applied to the nasal passages, and a balloon catheter was advanced through one nostril into the lower esophagus. The animals were then intubated with a cuffed endotracheal tube through the other nostril with a flexible fiberoptic bronchoscope as a guide. All protocols were approved by the Mount Sinai Medical Center Animal Research Committee, which is responsible for assuring the humane care and use of experimental animals.

Airway Mechanics: Breath-by-breath determination of mean pulmonary flow resistance (RL) was measured with the esophageal balloon technique previously described (Abraham et al, (1994), J. Clin. Invest., v. 93, p. 776 and (1997), Am. J. Respir. Crit. Care Med., v. 156, p. 696). The mean of at least 5 breaths, free of swallowing artifact, were used to obtain RL in cm H2O/L/s. Immediately after the measurement of RL, thoracic gas volume (Vtg) was measured in a constant-volume body plethysmograph to obtain specific lung resistance (SRL=RL×Vtg) in cm H2O.s1.

Aerosol Delivery Systems: All aerosols were generated using a disposable medical nebulizer (Raindrop; Puritan Bennett, Lenexa, Kans.) that provided an aerosol with a mass median aerodynamic diameter of 3.2 µm as determined by an Andersen cascade impactor. The nebulizer was connected to a dosimeter system, consisting of a solenoid valve and a source of compressed air (20 psi). The output of the nebulizer was directed into a plastic T-piece, one end of which was connected to the inspiratory port of a piston respirator (Harvard Apparatus, Mills, Mass.). The solenoid valve was activated for 1 s at the beginning of the inspiratory cycle of the respirator. Aerosols were delivered at a tidal volume of 500 ml and a rate of 20 breaths/min as previously described (Abraham et al, 1994; 1997 supra).

Concentration Response Curves to Carbachol Aerosol: Airway responsiveness was determined from cumulative concentration response curves to carbachol inhaled as previously described. $SR_L$ was measured immediately after inhalation of phosphate-buffered saline (PBS) and after each consecutive administration of 10 breaths of increasing concentrations of carbachol (0.25, 0.5, 1.0, 2.0, and 4.0% wt/vol PBS). The provocation test was discontinued when $SR_L$ increased over 400% from the post-PBS value or after the highest carbachol concentration had been administered. The cumulative carbachol concentration (in breath units [BU]) that increased $SR_L$ by 400% over the post-PBS value (PC400) was calculated by interpolation from the dose-response curve. One BU was defined as one breath of a 1% wt/vol carbachol aerosol solution (Abraham et al, 1994; 1997 supra).

Antigen Challenge: A. suum extract (Greer Diagnostics, Lenoir, N.C.) was diluted with PBS to a concentration of 82,000 protein nitrogen units/ml and delivered as an aerosol (20 breaths/min×20 min).

Carbamylcholine (Carbachol; Sigma Chemical Co., St. Louis, Mo.) was dissolved in PBS at concentrations of 0.25, 0.50, 1.0, 2.0, and 4.0% wt/vol and delivered as an aerosol. Peptides were dissolved in 0.9% saline prepared in 3 to 5 ml total volume depending on the route of administration (aerosol, oral or intravenously) for the study.

Figure 2:
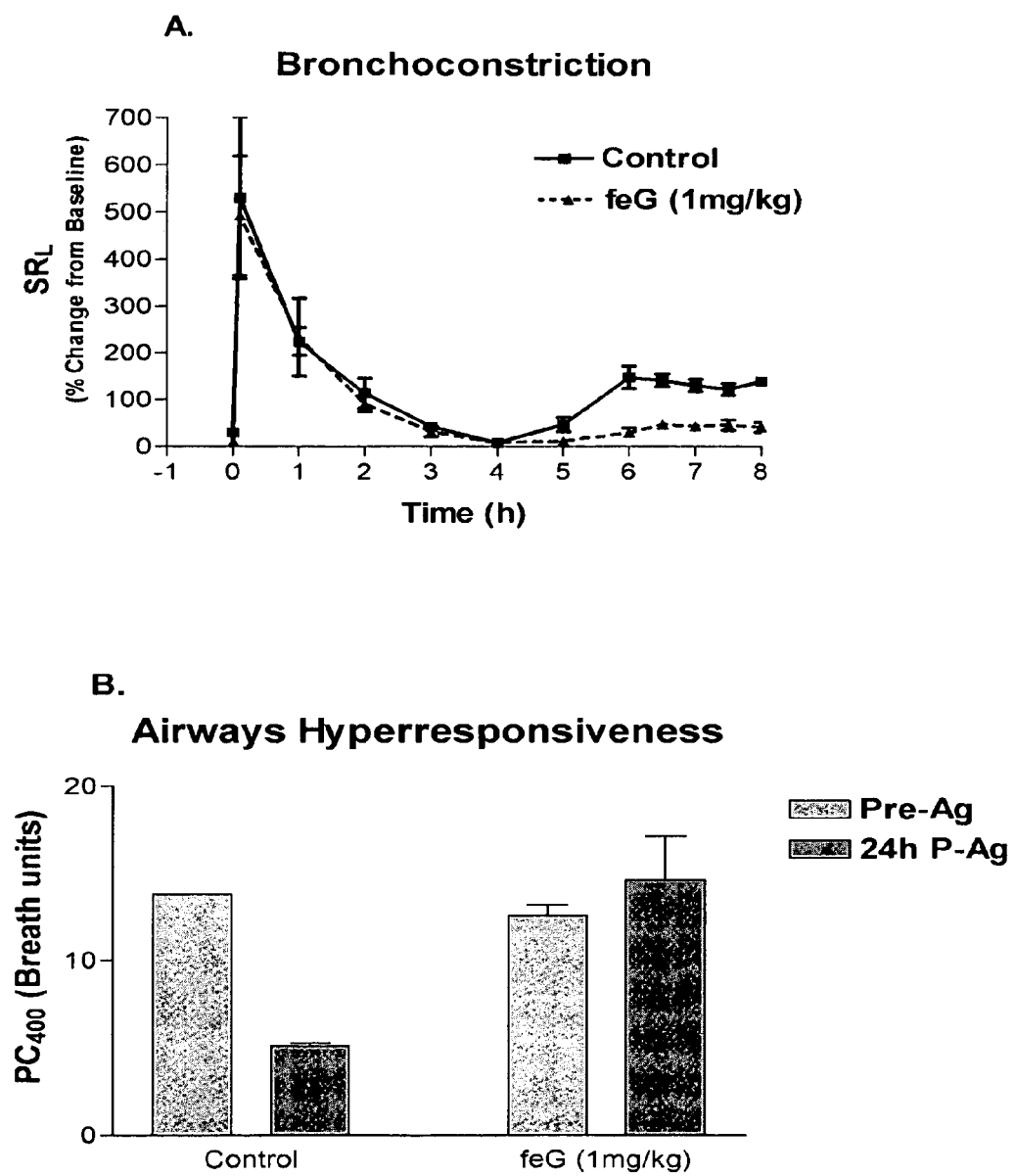
FIGS. 2A and 2B show the effect of intravenous treatment with feG on antigen-induced airway responses in sheep expressed as in FIGS. 1A and 1B.
Figure 3:
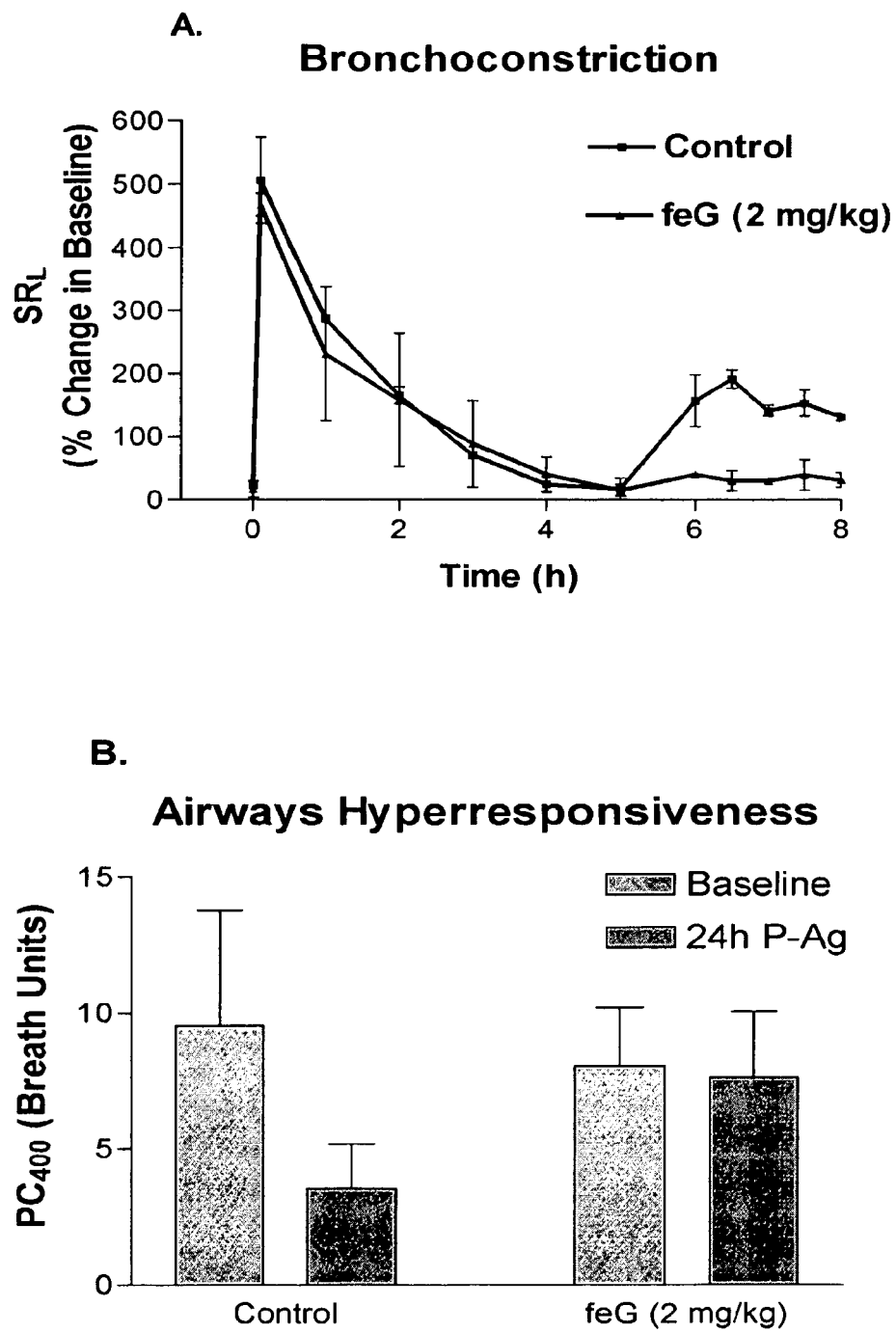
FIGS. 3A and 3B show the effect of two oral pre-challenge treatments with feG on antigen-induced airway responses in sheep expressed as in FIGS. 1A and 1B.
Figure 4:
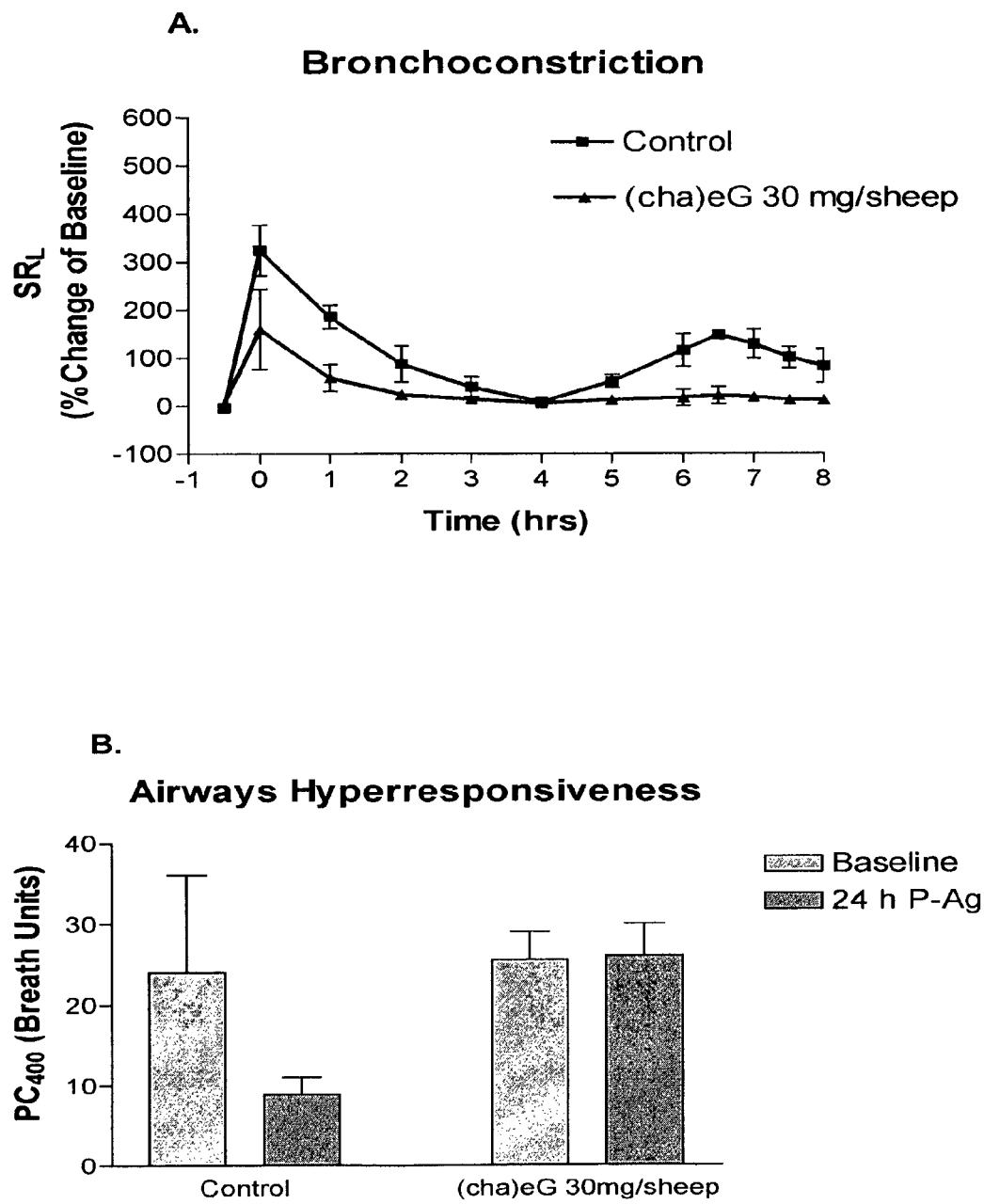
FIGS. 4A and 4B show the effect of aerosol treatment with (cha)eG on antigen-induced airway responses in sheep expressed as in FIGS. 1A and 1B.
Figure 5:
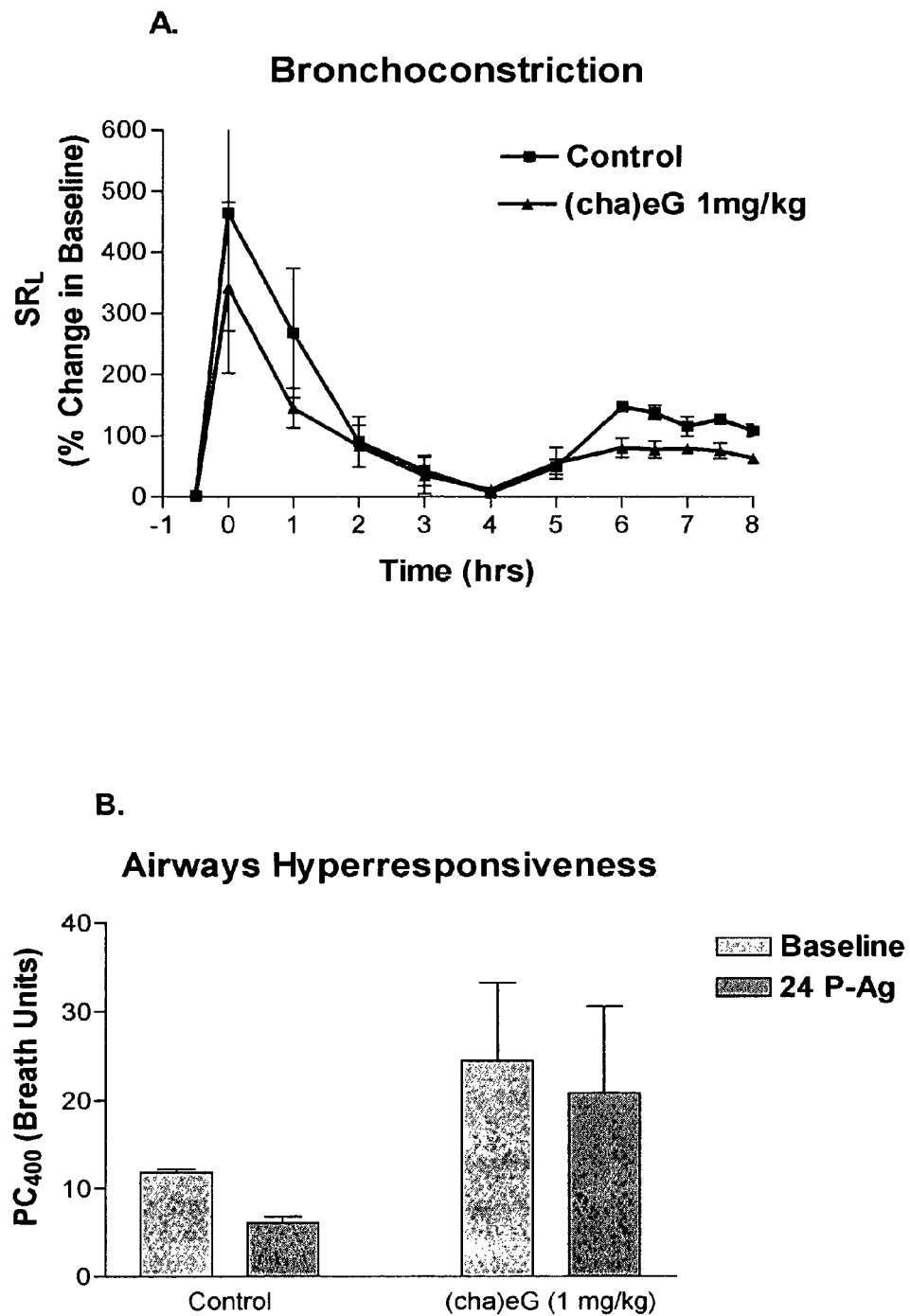
FIGS. 5A and 5B show the effect of intravenous treatment with (cha)eG on antigen-induced airway responses in sheep expressed as in FIGS. 1A and 1B.
Figure 6:
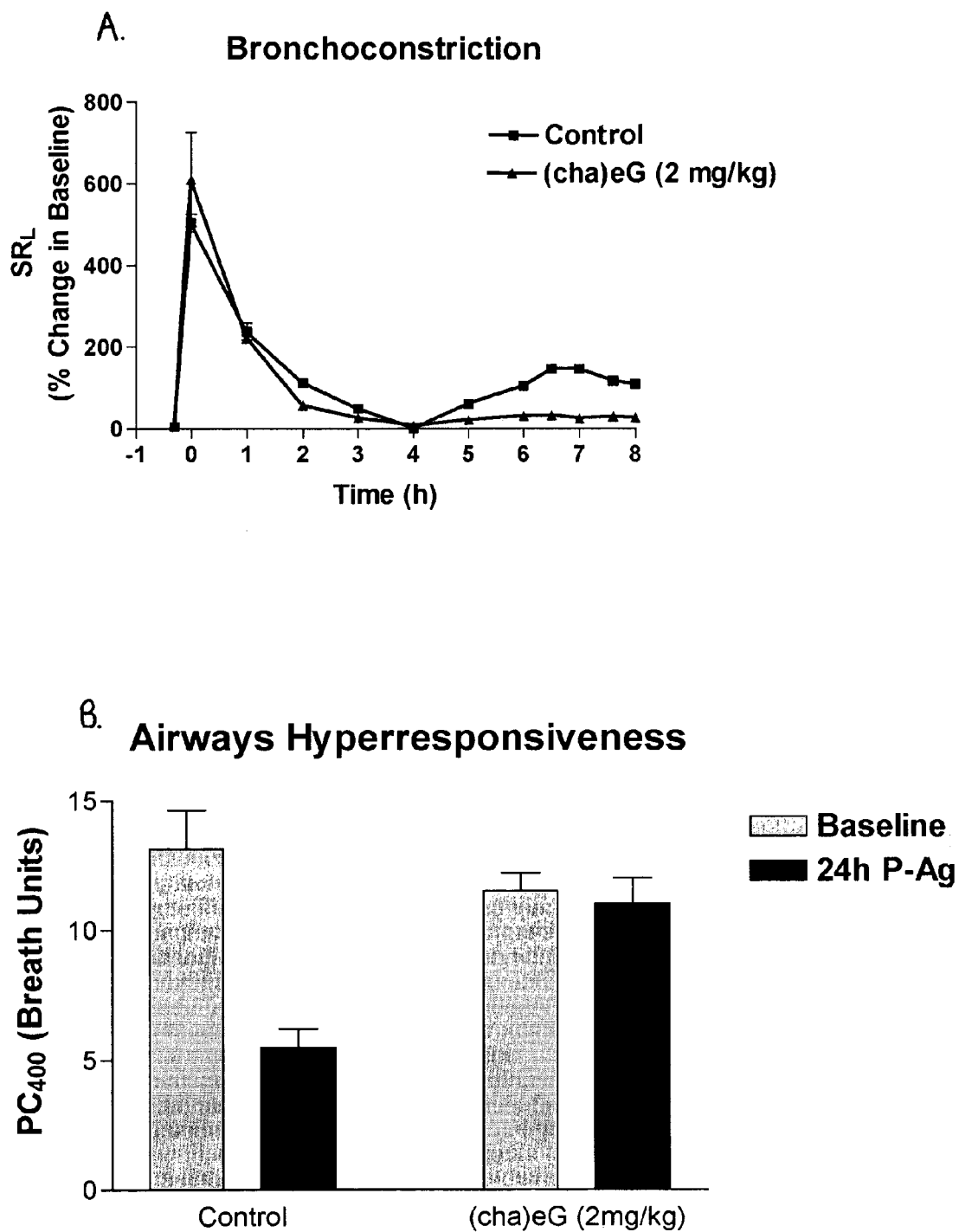
FIGS. 6A and 6B show the effect of two oral pre-challenge treatments with (cha)eG on antigen-induced airway responses in sheep expressed as in FIGS. 1A and 1B.
Figure 7:
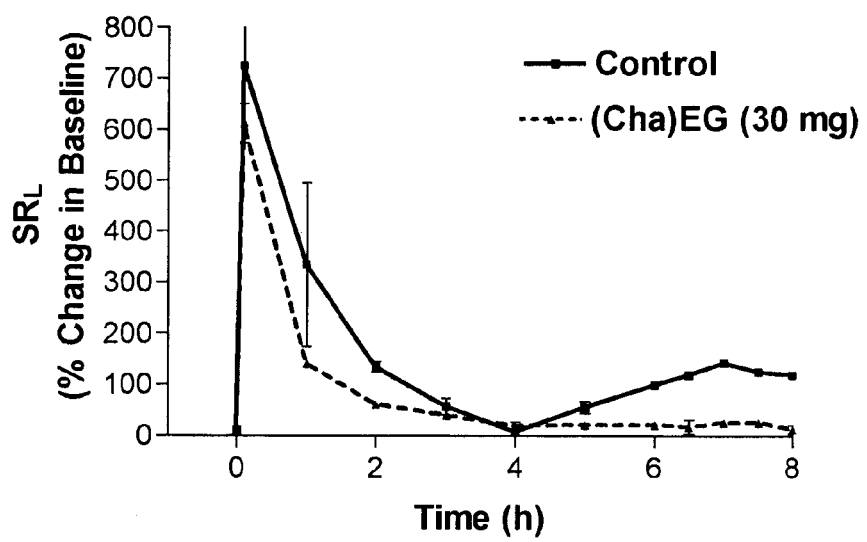
FIGS. 7A and 7B show the effect of aerosol treatment with (Cha)EG on antigen-induced airway responses in sheep expressed as in FIGS. 1A and 1B.
Figure 7:
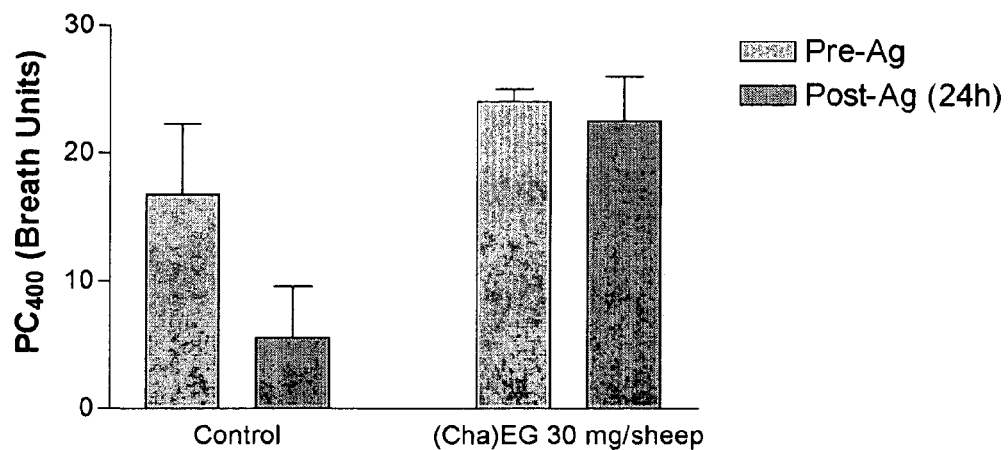
Figure 8:
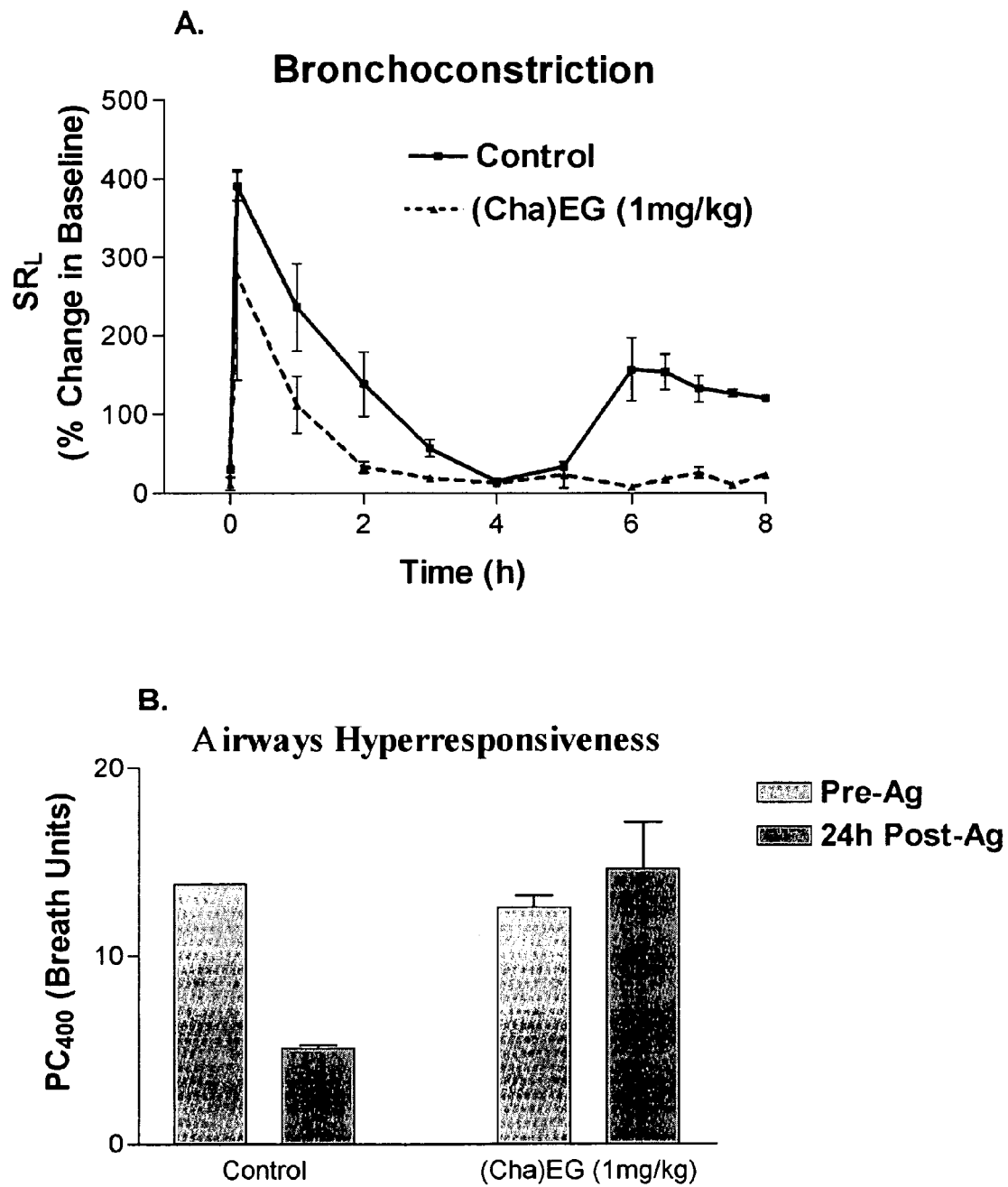
FIGS. 8A and 8B show the effect of intravenous treatment with (Cha)EG on antigen-induced airway responses in sheep expressed as in FIGS. 1A and 1B.

Experimental Trials: Each sheep was subjected to a control trial in which a placebo (PBS without additive) was used as the test pretreatment before allergen challenge with *Ascaris suum* antigen. Subsequently, the sheep were pretreated, prior to allergen challenge, with a test peptide (prepared by Core Laboratories) in sterile, endotoxin-free PBS, as follows:

(i) feG (30 mg/sheep) was given by aerosol 20 min. before challenge with antigen.
FIG. 1A shows bronchoconstriction and FIG. 1B shows airway hyperresponsiveness, after antigen challenge.
(ii) feG (1 mg/kg) was given intravenously 20 min. before antigen challenge.
FIG. 2A shows bronchoconstriction and FIG. 2B shows airway hyperresponsiveness, after antigen challenge.
(iii) feG was administered orally, at a dose of 2 mg/kg, at 24 h. and 30 min. before antigen challenge.
FIG. 3A shows bronchoconstriction and FIG. 3B shows airway hyperresponsiveness, after antigen challenge.
(iv) (cha)eG (30 mg/sheep) was given by aerosol 20 min. before antigen challenge.
FIG. 4A shows bronchoconstriction and FIG. 4B shows airway hyperresponsiveness, after antigen challenge.
(v) (cha)eG (1 mg/kg) was given intravenously 20 min before antigen challenge.
FIG. 5A shows bronchoconstriction and FIG. 5B shows airway hyperresponsiveness, after antigen challenge.
(vi) (cha)eG was administered orally, at a dose of 2 mg/kg, at 24 h and 30 min before antigen-challenge.
FIG. 6A shows bronchoconstriction and FIG. 6B shows airway hyperresponsiveness, after antigen challenge.
(vii) (Cha)EG (30 mg/sheep) was given by aerosol 20 min before challenge with antigen
FIG. 7A shows bronchoconstriction and FIG. 7B shows airway hyperresponsiveness, after antigen challenge.
(viii) (Cha)EG (1 mg/kg) was given intravenously 20 min before antigen challenge.
FIG. 8A shows bronchoconstriction and FIG. 8B shows airway hyperresponsiveness, after antigen challenge.

Activity of analogue peptides was compared with activity of feG.

Sheep that had received a total dose of 30 mg of feG by aerosol inhalation, 20 min before antigen challenge, exhibited attenuation of 78% and 89%, respectively, of the early (0-3 h) and the late (6-8 h) bronchoconstriction provoked by aerosol administration of *Ascaris suum* antigen. This peptide also reduced the increase in airway hyperresponsiveness to methacholine with a 1.9-fold lower dose producing a $PC_{400}$ response.

Sheep that had received a dose of 1 mg/kg of feG given intravenously, 20 min before antigen challenge, exhibited an attenuation of 72% of the late (6-8 h) bronchoconstriction provoked by aerosol administration of *Ascaris suum* antigen. The early bronchoconstrictor phase was not affected. Intravenous treatment with feG also reduced the increase in airways hyperresponsiveness to methacholine with a 2.2-fold lower dose producing a $PC_{400}$ response.

Sheep that had received feG orally, in two doses of 2 mg/kg, 24 h and 30 min before intravenous antigen challenge, exhibited an attenuation of 69% of the late (6-8 h) bronchoconstriction provoked by aerosol administration of *Ascaris suum* antigen. The early bronchoconstrictor phase was not affected. Intravenous treatment with feG also reduced the increase in airways hyperresponsiveness to methacholine with a 2.1-fold lower dose producing a $PC_{400}$ response.

Sheep that had received a total dose of 30 mg of (cha)eG by aerosol, 20 min before antigen challenge, exhibited attenuation of 64% and 88%, respectively, of the early (0-3 h) and the late (6-8 h) bronchoconstriction provoked by aerosol administration of *Ascaris suum* antigen. Aerosol treatment with (cha)eG also reduced the increase in airways hyperresponsiveness to methacholine with a 2.8-fold lower dose producing a $PC_{400}$ response.

Sheep that had received a dose of 1 mg/kg of (cha)eG given intravenously, 20 min before antigen challenge, exhibited attenuation of 58% and 43%, respectively, of the early (0-3 h) and the late (6-8 h) bronchoconstriction provoked by aerosol administration of *Ascaris suum* antigen. This peptide also reduced the increase in airways hyperresponsiveness to methacholine with a 1.7-fold lower dose producing a $PC_{400}$ response.

Sheep that had received (cha)eG orally in two doses of 2 mg/kg, 24 h and 30 min before antigen challenge intravenously, exhibited an attenuation of 58% and 43%, respectively, of the early (0-3 h) and the late (6-8 h) bronchoconstriction provoked by aerosol administration of *Ascaris suum* antigen. When administered orally (cha)eG reduced the increase in airway hyperresponsiveness to methacholine with a 1.7-fold lower dose producing a $PC_{400}$ response.

Sheep that received a total dose of 30 mg of (Cha)EG by aerosol inhalation, 20 min before antigen challenge, exhibited attenuation of 52% and 84%, respectively, of the early (0-3 h) and the late (6-8 h) bronchoconstriction provoked by aerosol administration of *Ascaris suum* antigen. This peptide, (Cha)EG, reduced the increase in airway hyperresponsiveness to methacholine with a 1.9-fold lower dose producing a $PC_{400}$ response.

Sheep that received a dose of 1 mg/kg of (Cha)EG intravenously, 20 min before antigen challenge, exhibited attenuation of 62% and 67%, respectively, of the early (0-3 h) and the late (6-8 h) bronchoconstriction provoked by aerosol administration of *Ascaris suum* antigen. This peptide, (Cha)EG, reduced the increase in airway hyperresponsiveness to methacholine with a 3.2-fold lower dose producing a $PC_{400}$ response.

Example 3

Inhibition of Antibody-Mediated Vascular Permeability and Active Cutaneous Anaphylaxis in Rats For this in vivo study, peptides were prepared by conventional by Core Laboratories, Queen's University, Kingston, Ontario, and examined for their inhibitory effects on an vascular permeability elicited by IgG- or IgE-antibodies and on active cutaneous anaphylactic (ACA) reactions. The IgG- or IgE-antibody reactions were studies in normal, unsensitized Sprague-Dawley rats anaethetized with sodium pentobarbital (65 mg/kg). The backs of the animals were shaved, and a 2×4 grid was drawn on the back in black ink and in the middle of each square 50 µl of different concentrations of peptide (10-12 to 10-7 moles/l) were injected intradermally. Saline was used as a control. For IgG-mediated reactions rats were injected intravenously, via the penile vein, with 10 mg/kg of ovalbumin and 20 mg/kg of Evans blue, ten min later the IgG antibody (mouse anti-ovalbumin) and after 3 h the area of the vascular leak, visualized by the blue spots, was calculated with the formula for the surface area of an ellipse. Similar procedures were applied for studying IgE-mediated vascular leak in that rats were injected intravenously with 20 mg/kg of Evans blue, and 10 min later an a monoclonal antibody against the heavy chain of the rat IgE receptor was injected intradermally.

ACA reactions were elicited by antigen injections into the dorsal skin of ovalbumin sensitized rats. Sprague-Dawley rats were sensitized to 1 mg ovalbumin (OA) and 50 ng pertussis toxin (Sigma Chemical, St. Louis, Mo.) (Kosckea et al, 1994). Four to six weeks following sensitisation, anti-OA IgE antibody titer was determined via passive cutaneous anaphylaxis and rats with an antibody titre of 1:32 were used. To perform ACA rats were anaethetized with sodium pentobarbital (65 mg/kg) and their backs shaved. A 2×4 grid was drawn on the back in black ink and in the middle of each square different concentrations of peptide (10-12 to 10-6 moles) in 50 µl were injected intradermally. Saline was used as a control. The animals were then injected, via the penile vein, with Evans blue (20 mg/kg), a dye that binds to albumin. Ten minutes after the first intradermal injection 50 µl of ovalbumin antigen (100 ug/ml) was injected into the same site as the saline or peptide. Within a few minutes of the antigen injection into a control site, a blueing of the skin begins to develop as the Evans Blue-albumin complex moves out of the blood vessel consequent to antigen activation of mast cells. Thirty minutes after the injection of antigen the size of the histamine induced wheal was measured using calipers.

Figure 9:
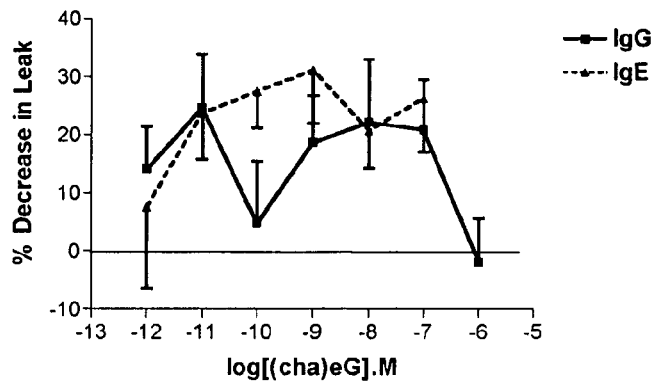
FIGS. 9A, 9B and 9C show the inhibitory effect of peptides of the invention on immunoglobulin-mediated vascular permeability in rats, expressed as % decrease in leak.
Figure 9:
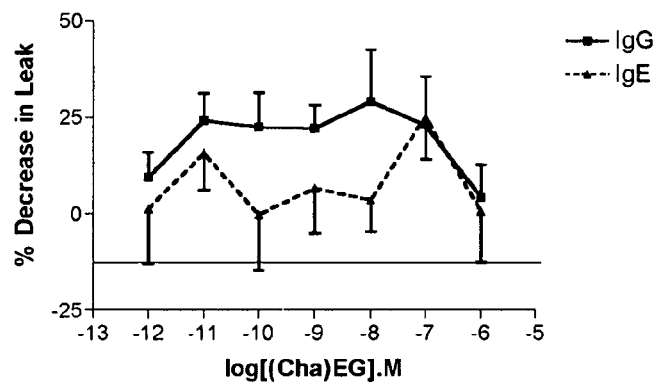
Figure 9:
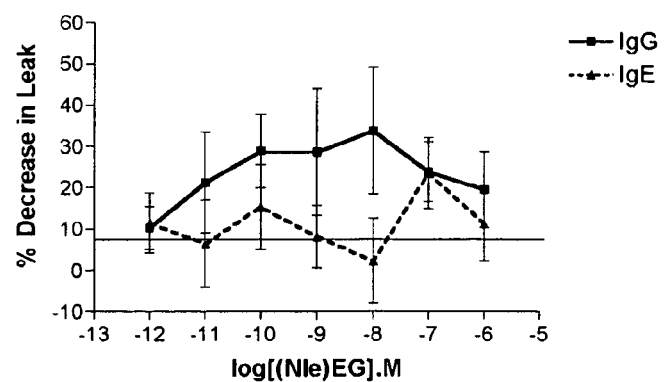
Figure 10:
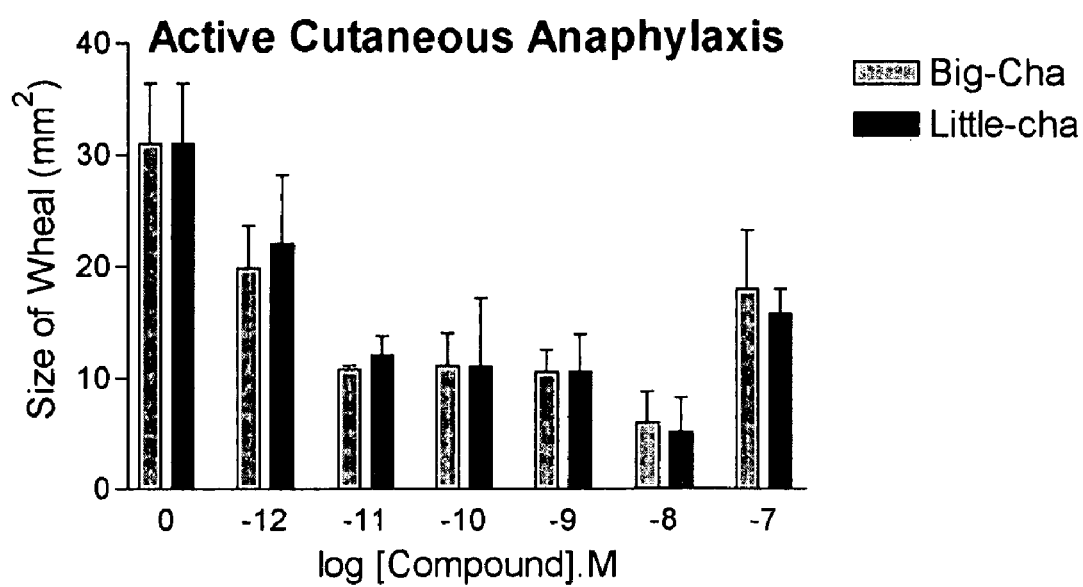
FIG. 10 shows the inhibitory effect of peptides of the invention on active cutaneous anaphylaxis in rats.

The results are shown in FIGS. 9 and 10.

Both (cha)eG (FIG. 9A), (Cha)EG (FIG. 9B), and (Nle)EG (FIG. 9C) inhibited the increase in vascular permeability (% decrease in vascular leak) elicited by either IgG- or IgE-antibodies, or of both of these antibodies. With all three peptides, the IgG-mediated vascular leak was inhibited more than the IgE-mediated vascular leak. However, at low concentrations ($10^{-11}$M to $10^{-9}$M) (cha)eG provided a significant inhibition of the IgE-mediated vascular leak. The ACA reaction was inhibited (reduced size of wheal) to a similar extent by both (Cha)EG and (cha)eG when injected at concentrations ranging from $10^{-11}$M to $10^{-8}$M (FIG. 10).

Example 4

Inhibition by (Cha)EG, MEG, fe(Sar) and fe of Allergen Induced Pulmonary Inflammation The Brown Norway rat/ovalbumin sensitization model of allergic asthma was used. These rats are high IgE producers and are widely used to study asthma because they develop an early and a late phase bronchoconstriction, as well as an increase in bronchial hyperresponsiveness.

Brown Norway rats (10-12 weeks old) were sensitized to ovalbumin (OA; Sigma Chemical Co. St. Louis, Mo.) with a 1 ml 0.9% saline ip injection containing 10 µg OA, 150 mg Al(OH)3 (ICN, Aurora, Ohio) and 50 ng *B. pertussis* toxin (Sigma). Twenty-one days post sensitization, experiments were performed under light anaesthesia. Animals were challenged with aerosolized OA (5%) and thirty minutes later they were given an oral treatment with either test peptide ((Cha)EG, MEG, fe(Sar) or fe: 250 µg/kg) or saline (controls).

Twenty-four hours after allergen challenge, the rats were anaesthetised with pentobarbital (65 mg/kg) and cells were collected from the lower respiratory tract by bronchoalveolar lavage (BAL). The abdomen was opened, and the diaphragm was cut to relieve intrathoracic pressure. A tracheotomy was performed and a cannula inserted to the first bifurcation of the bronchioles. The bronchioles and alveoli were washed 10 times with 5 ml of phosphate-buffered saline (PBS). The cells were centrifuged at 200 g for 20 min and then resuspended in 1 ml of PBS. The total number of cells were counted and differentials determined with May-Grunwald/Giesma stain.

The control rats responded to the aerosol challenge with 5% sensitizing antigen ovalbumin (OA) with a substantial pulmonary inflammation at 24 h. The total number of cells recovered by bronchoalveolar lavage from the alveolar spaces increased from 3.5±1.8 ($\times 10^6$) cells in sensitized, unchallenged, rats to 25.0±3.2 ($\times 10^6$) in sensitized, antigen-challenged rats. (Cha)EG, MEG, fe(Sar) and fe (0.25 mg/kg), when administered 30 min following allergen challenge of sensitized rats, significantly reduced the total cell number recovered by bronchoalveolar lavage by 50% to 80%, to 8.8±3.5 ($\times 10^6$), 12.1±3.6 ($\times 10^6$), 5.1×2.6 ($\times 10^6$) and 13.1±3.7 ($\times 10^6$) respectively.

The present invention is not limited to the features of the embodiments described herein, but includes all variations and modifications within the scope of the claims.

TABLE 1

Structure Activity Relationships for Tri- and Di-Amino Acid Peptides.

| Primary Substitution | Peptide | Avg | SEM | Significance |
|---|---|---|---|---|
|  | Control | 0.267 | 0.020 |  |
| L-Phe | FEG | 0.125 | 0.040 | * |
| D-phe-D-glu | feG | 0.138 | 0.019 | * |
| D-phe-D-glu-D-ala | fea | 0.128 | 0.018 | * |

TABLE 1-continued

Structure Activity Relationships for Tri- and Di-Amino Acid Peptides.

| Primary Substitution | Peptide | Avg | SEM | Significance |
|---|---|---|---|---|
| D-tyr-D-glu | yeG | 0.157 | 0.010 | * |
| L-Phg | (Phg)EG | 0.136 | 0.023 | * |
| L-Trp | WEG | 0.128 | 0.052 | * |
| L-Trp-L-Asp | WDG | 0.158 | 0.024 | * |
| NMePhe | (NMeF)EG | 0.118 | 0.027 | * |
| L-Nle | (Nle)EG | 0.127 | 0.027 | * |
| L-Cha | (Cha)EG | 0.092 | 0.014 | * |
| L-Met | MEG | 0.121 | 0.027 | * |
| L-Met (position 3) | FEM | 0.081 | 0.016 | * |
| L-Ile (position 3) | FEI | 0.161 | 0.018 | * |
| β-alanine (position 3) | FE-Ba | 0.091 | 0.012 | * |
| Sarcosine (position 3) | FESar | 0.160 | 0.034 | * |
| γAbu (position 3) | FE(γAbu) | 0.130 | 0.050 | * |
| Dipeptide | FE | 0.105 | 0.014 | * |
| Dipeptide: D-phe-D-glu | fe | 0.161 | 0.010 | * |
| Dipeptide: D-cha-D-glu | (cha)e | 0.189 | 0.020 | * |
| L-Tyr | YEG | 0.306 | 0.032 | NS |
| L-Phe-L-Asp | FDG | 0.262 | 0.042 | NS |
| D-Phe-D-Asp | fdG | 0.395 | 0.105 | NS |
| L-Tyr-L-Asp | YDG | 0.221 | 0.106 | NS |
| D-Tyr-D-Asp | ydG | 0.208 | 0.083 | NS |
| D-Trp-D-Glu | weG | 0.201 | 0.047 | NS |
| D-Trp-D-Asp | wdG | 0.200 | 0.043 | NS |
| Dipeptide: L-Glu-Gly | EG | 0.242 | 0.085 | NS |
| L-Glu | EEG | 0.230 | 0.015 | NS |
| Gly | GEG | 0.202 | 0.081 | NS |
| L-Ala | AEG | 0.252 | 0.106 | NS |
| L-Leu | LEG | 0.196 | 0.050 | NS |
| L-Ile | IEG | 0.222 | 0.070 | NS |
| L-Val | VEG | 0.313 | 0.030 | NS |
| L-Nval | (Nval)EG | 0.191 | 0.082 | NS |
| L-Thr | TEG | 0.250 | 0.042 | NS |
| L-Cys | CEG | 0.247 | 0.107 | NS |
| L-His | HEG | 0.195 | 0.028 | NS |
| L-Asp | NEG | 0.384 | 0.122 | NS |
| L-Arg | REG | 0.220 | 0.047 | NS |
| L-Pro | PEG | 0.324 | 0.072 | NS |
| L-Ala | FAG | 0.171 | 0.040 | NS |
| L-Gln | FQG | 0.309 | 0.050 | NS |
| L-Asp | FDG | 0.262 | 0.042 | NS |
| D-Tyr-D-Asp | ydG | 0.208 | 0.083 | NS |
| L-Lys | FKG | 0.183 | 0.027 | NS |
| L-Arg | FRG | 0.160 | 0.025 | NS |
| L-His | FHG | 0.167 | 0.050 | NS |
| L-Hse (position 2) | F(Hse)G | 0.258 | 0.050 | NS |
| Pro (position 3) | FEP | 0.246 | 0.021 | NS |
| L-Ala (position 3) | FEA | 0.217 | 0.046 | NS |
| L-Nval | FE(Nval) | 0.241 | 0.037 | NS |
| L-Gln | FEQ | 0.310 | 0.046 | NS |
| L-Thr | FET | 0.237 | 0.054 | NS |
| L-Glu | FEE | 0.318 | 0.056 | NS |
| L-Lys | FEK | 0.252 | 0.056 | NS |
| L-Arg | FER | 0.134 | 0.023 | NS |
| L-His | FEH | 0.200 | 0.035 | NS |
| L-Cys | FEC | 0.187 | 0.023 | NS |
|  | Ac-FEG | 0.173 | 0.046 | NS |
|  | FEG-NH$_2$ | 0.262 | 0.081 | NS |

NS = not significant
* = significant inhibition

I claim:

1. A method of inhibiting an inflammatory reaction in a mammal comprising administering to the mammal an effective amount of a peptide of the formula:
$X^1$-$X^2$-$X^3$ wherein $X^1$ is selected from the group consisting of 2-amino-hexanoic acid; 2-amino-heptanoic acid; 2-amino-octanoic acid; and cyclohexyl-substituted 2-amino-ethanoic acid, 2-amino-propanoic acid or 2-amino-butanoic acid;
$X^2$ is an acidic amino acid; and
$X^3$ is an aliphatic amino acid,
wherein the C-terminal peptide of the peptide, $X^3$, is optionally amidated and the amide of the N-terminal amino acid of the peptide, $X^1$, is optionally lower alkyl-substituted.

2. The method of claim 1, wherein at least one amino acid of the peptide is a D-amino acid.

3. The method of claim 1, wherein the amide of the N-terminal amino acid of the peptide, $X^1$, is lower alkyl-substituted.

4. The method of claim 1, wherein the amide of the N-terminal amino acid of the peptide, $X^1$, is methylated.

5. The method of claim 1, wherein the C-terminal amino acid of the peptide, $X^3$, is amidated.

6. The method of claim 1, wherein the administered peptide is L-cyclohexylalanine-L-glutamic acid-glycine.

7. The method of claim 1, wherein the administered peptide is D-cyclohexylalanine-D-glutamic acid-glycine.

8. The method of claim 1, wherein the inflammatory reaction is associated with a disorder selected from the group consisting of asthma, rhinitis, conjunctivitis, atopic dermatitis and intestinal anaphylaxis.

9. The method of claim 1, wherein the inflammatory reaction is due to non-allergen factors.

10. The method of claim 1, wherein the inflammatory reaction is associated with intrinsic asthma.

11. The method of claim 1, wherein the inflammatory reaction is a Type I, Type II or Type III hypersensitivity reaction.

12. The method of claim 1, wherein the inflammatory reaction is an immunological reaction.

13. The method of claim 1, wherein the mammal is a human.

14. A method of inhibiting an inflammatory reaction in a mammal comprising administering to the mammal an effective amount of a peptide of the formula: $X^1$-$X^2$-$X^3$ wherein
$X^1$ is selected from the group consisting of 2-amino-hexanoic acid; 2-amino-heptanoic acid; 2-amino-octanoic acid; and cyclohexyl-substituted 2-amino-ethanoic acid, 2-amino-propanoic acid or 2-amino-butanoic acid; and methionine;
$X^2$ is glutamic acid; and
$X^3$ is an aliphatic amino acid,
wherein the C-terminal peptide of the peptide, $X^3$, is optionally amidated and the amide of the N-terminal amino acid of the peptide, $X^1$, is optionally lower alkyl-substituted.

15. The method of claim 14,
wherein $X^1$ is selected from the group consisting of 2-amino-hexanoic acid, 2-amino-heptanoic acid, 2-amino-octanoic acid, 2-amino-2-cyclohexyl ethanoic acid, 2-amino-3-cyclohexyl propanoic acid, 2-amino-3-cyclohexyl butanoic acid, 2-amino-4-cyclohexyl butanoic acid and methionine;
and
$X^3$ is selected from the group consisting of glycine, methionine, isoleucine, alanine, β-alanine, sarcosine and γ-aminobutyric acid.

16. The method of claim 15, wherein $X^1$ is selected from the group consisting of 2-amino-3-cyclohexyl propanoic acid (cyclohexylalanine), 2-amino-hexanoic acid (norleucine) and methionine.

17. A method of inhibiting an inflammatory reaction in a mammal comprising administering to the mammal an effective amount of a peptide selected from the group consisting of:
(a) L-cyclohexylalanine-L-glutamic acid-glycine;
(b) D-cyclohexylalanine-D-glutamic acid-glycine;

(c) L-norleucine-L-glutamic acid-glycine;
(d) D-norleucine-D-glutamic acid-glycine;
(e) L-methionine-L-glutamic acid-glycine;
(f) D-methionine-D-glutamic acid-glycine;
(g) L-cyclohexylalanine-L-glutamic acid-L-methionine;
(h) D-cyclohexylalanine-D-glutamic acid-L-methionine;
(i) L-cyclohexylalanine-L-glutamic acid-L-isoleucine; and
(j) D-cyclohexylalanine-D-glutamic acid-D-isoleucine.

18. A method of treating asthma in a mammal comprising administering to the mammal an effective amount of a peptide of the formula:

$X^1$-$X^2$-$X^3$ wherein $X^1$ is selected from the group consisting of 2-amino-hexanoic acid; 2-amino-heptanoic acid; 2-amino-octanoic acid; and cyclohexyl-substituted 2-amino-ethanoic acid, 2-amino-propanoic acid or 2-amino-butanoic acid; and methionine;

$X^2$ is an acidic amino acid; and $X^3$ is an aliphatic amino acid wherein the C-terminal peptide of the peptide, $X^3$, is optionally amidated and the amide of the N-terminal amino acid of the peptide, $X^1$, is optionally lower alkyl-substituted.

19. The method of claim 18, wherein the administered peptide is of the formula $X^1$-$X^2$-$X^3$ wherein $X^1$ is selected from the group consisting of 2-amino-hexanoic acid, 2-amino-heptanoic acid, 2-amino-octanoic acid, 2-amino-2-cyclohexyl ethanoic acid, 2-amino-3-cyclohexyl propanoic acid, 2-amino-3-cyclohexyl butanoic acid, 2-amino-4-cyclohexyl butanoic acid and methionine;

$X^2$ is glutamic acid; and $X^3$ is selected from the group consisting of glycine, methionine, isoleucine, alanine, β-alanine, sarcosine and γ-aminobutyric acid.

20. The method of claim 19, wherein $X^1$ is selected from the group consisting of 2-amino-3-cyclohexyl propanoic acid (cyclohexylalanine), 2-amino-hexanoic acid (norleucine) and methionine.

21. The method of claim 18, wherein at least one amino acid of the peptide is a D-amino acid.

22. The method of claim 18, wherein the amide of the N-terminal amino acid of the peptide, $X^1$, is lower alkyl-substituted.

23. The method of claim 18, wherein the amide of the N-terminal amino acid of the peptide, $X^1$, is methylated.

24. The method of claim 18, wherein the C-terminal amino acid of the peptide, $X^3$, is amidated.

25. The method of claim 18, wherein the administered peptide is selected from the group consisting of
(a) L-cyclohexylalanine-L-glutamic acid-glycine;
(b) D-cyclohexylalanine-D-glutamic acid-glycine;
(c) L-norleucine-L-glutamic acid-glycine;
(d) D-norleucine-D-glutamic acid-glycine;
(e) L-methionine-L-glutamic acid-glycine;
(f) D-methionine-D-glutamic acid-glycine;
(g) L-cyclohexylalanine-L-glutamic acid-L-methionine;
(h) D-cyclohexylalanine-D-glutamic acid-L-methionine;
(i) L-cyclohexylalanine-L-glutamic acid-L-isoleucine; and
(j) D-cyclohexylalanine-D-glutamic acid-D-isoleucine.

26. The method of claim 18, wherein the administered peptide is L-cyclohexylalanine-L-glutamic acid-glycine.

27. The method of claim 18, wherein the administered peptide is D-cyclohexylalanine-D-glutamic acid-glycine.

* * * * *